United States Patent
Bhardwaj et al.

(10) Patent No.: US 8,207,222 B2
(45) Date of Patent: Jun. 26, 2012

(54) NITRIC OXIDE RELEASING DERIVATIVES OF PARACETAMOL

(75) Inventors: Tilak Raj Bhardwaj, Chandigarh (IN); Manoj Kumar, Chandigarh (IN); Necraj Mehta, Chandigarh (IN); Neelima Dhingra, Chandigarh (IN)

(73) Assignee: Council of Scientific and Industrial Research, New Delhi (IN)

( * ) Notice: Subject to any disclaimer, the term of this patent is extended or adjusted under 35 U.S.C. 154(b) by 104 days.

(21) Appl. No.: 12/707,410

(22) Filed: Feb. 17, 2010

(65) Prior Publication Data

US 2010/0234472 A1 Sep. 16, 2010

Related U.S. Application Data

(63) Continuation-in-part of application No. PCT/IN2008/000514, filed on Aug. 14, 2008.

(30) Foreign Application Priority Data

Aug. 17, 2007 (IN) .......................... 1753/DEL/2007

(51) Int. Cl.
*C07C 203/04* (2006.01)
*A61K 31/167* (2006.01)

(52) U.S. Cl. ........................................ 514/509; 558/482
(58) Field of Classification Search ................... 558/482; 514/509

See application file for complete search history.

(56) References Cited

FOREIGN PATENT DOCUMENTS

| WO | 01/12584 A | 2/2001 |
|---|---|---|
| WO | 02/30866 A | 4/2002 |
| WO | 03/084550 A | 10/2003 |
| WO | 2005/054175 A | 6/2005 |

OTHER PUBLICATIONS

E.A. Romero-Sandoval, M.M. Curros-Criado, G. Gaitan, C. Molina, J.F. Herrero: "Nitroparacetamol (NCX-701) and Pain: First in a Series of Novel Analgesics" CNS Drug Review, vol. 13, Aug. 9, 2007; pp. 279-295, XP002506074 the whole document.

*Primary Examiner* — Jason M Nolan
(74) *Attorney, Agent, or Firm* — Ladas & Parry LLP

(57) ABSTRACT

The present invention particularly relates to novel nitrate esters of paracetamol. The nitrate esters of paracetamol are prepared by reacting the paracetamol with dihaloalkyl compound and followed by reaction with silver nitrate to obtain the corresponding nitrate ester derivatives. The nitrate esters of paracetamol are useful as analgesic, anti-inflammatory agents.

13 Claims, 3 Drawing Sheets

NITRIC OXIDE RELEASING DERIVATIVES OF PARACETAMOL

This is a continuation in part of copending International Application PCT/IN2008/000514 filed on Aug. 14, 2008, which designated the U.S., claims the benefit thereof and incorporates the same by reference.

FIELD OF THE INVENTION

The present invention relates to nitric oxide releasing derivatives of paracetamol. The present invention particularly relates to novel nitrate esters of paracetamol. The present invention pertains to process of preparation of nitrate esters of paracetamol. More particularly, the invention relates to nitric oxide releasing derivatives of paracetamol which show better analgesic and anti-inflammatory activities and decreased liver toxicities as apparent from their biochemical and histopathologic profile.

BACKGROUND OF THE INVENTION

Paracetamol (paracetamol, 1) is among most commonly used analgesics. It effectively reduces fever and mild-to moderate pain, and is regarded, in general, as a very safe drug. Nevertheless, overdose (deliberate) is a common cause of hepatic injury, accounting for ~40% of cases of acute liver failure in the USA. [Wu, C. C. Nitric oxide and inflammation. *Curr. Med. Chem.-Anti-inflammatory & anti-allergy agents*, 2004, 3, 217-222; Joshi, G. P. NCX-701. NicOx. *Curr. Opin. Investig. Drugs*, 2004, 5, 755-759; and Moore, P. K.; Marshall, M. Nitric oxide releasing paracetamol (nitroparacetamol). *Dig. Liver Dis.*, 2003, 35.] It is an effective analgesic and antipyretic agent and unlike other NSAIDs (Non-steroidal Anti-inflammatory Drugs) has been reported to have little anti-inflammatory effects. [Fiorucci, S.; Antonelli, E.; Mencarelli, A.; Palazzetti, B.; Alvarez-Miller, L.; Muscara, M.; del Soldato, P.; Sanpaolo, L.; Wallace, J. L.; Morelli, A. A NO-releasing derivative of paracetamol spares the liver by acting at several checkpoints in the Fas pathway. *Br. J. Pharmacol.*, 2002, 135, 589-599.] It is metabolized in liver by three pathways-glucuronidation, sulfonation (both accounting for 95% of metabolism) or via cytochrome P450 enzyme system (5%) in which it is converted to a toxic metabolite (N-acetyl-p-benzoquinone imine, 2) which further is rendered harmless through an interaction with the endogenous antioxidant glutathione.

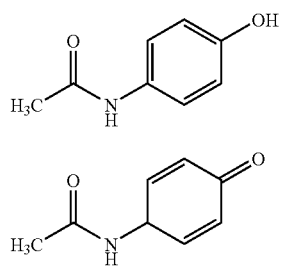

But overproduction of this toxic metabolite leads to depletion of glutathione stores in liver and further accumulation of the toxic metabolite causes tissue injury and cell death. [Futter, L. E.; al-Swayeh, O. A.; Moore, P. K. A comparison of the effect of nitroparacetamol and paracetamol on liver injury. *Br. J. Pharmacol.*, 2000, 132, 10-12.] Numerous derivatives of paracetamol have been synthesized to get a safer non-hepatotoxic drug. One of the major achievements has been by Nocox in Italy. It has designed NCX-701 (3) by adding NO moiety to paracetamol, via an aliphatic spacer to improve the anti-inflammatory activity of paracetamol, based on the well-demonstrated activity of NO on cytokine synthesis and regulation of proinflammatory mediators. [Wallace, J. L. Paracetamol hepatotoxicity: NO to the rescue. *Br. J. Pharmacol.*, 2004, 143, 1-2.]

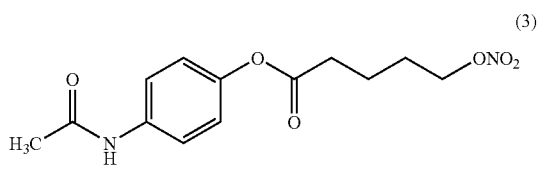

NO may modulate spinal and sensory neuron excitability through multiple mechanisms that may improve the antinociceptive activity of paracetamol. The pharmacological profile of NCX 701 has been reviewed. [Marshall, M.; Moore, P. K. Effect of nitric oxide releasing paracetamol and flurbiprofen on cytokine production in human blood. *Eur. J. Pharmacol.*, 2004, 483, 317-322; and al-Swayeh, O. A.; Futter, L. E.; Clifford, R. H.; Moore, P. K. Nitroparacetamol exhibits anti-inflammatory and anti-nociceptive activity. *Br. J. Pharmacol.*, 2000, 130, 1453-1456]. Compared with NSAIDs, paracetamol possesses little anti-inflammatory activity in humans and it does not induce damage of the gastric mucosa, but it could cause liver damage (or even poisoning) when used in high dosage. The aim of coupling paracetamol with NO has, therefore, been to improve its anti-inflammatory activity, and also to exploit the cytoprotective properties of NO to reduce potential liver damage. Concerning safety, several studies have highlighted the liver sparing profile of NCX 701 compared to paracetamol. The beneficial protective effect on the liver has been supposed to be related to the fact that NO can reduce the synthesis of several pro-inflammatory cytokines. [Wallace, J. L. Paracetamol hepatotoxicity: NO to the rescue. *Br. J. Pharmacol.*, 2004, 143, 1-2]. The anti-inflammatory activity related to NO release has been demonstrated in vitro and in vivo, [Marshall, M.; Moore, P. K. Effect of nitric oxide releasing paracetamol and flurbiprofen on cytokine production in human blood. *Eur. J. Pharmacol.*, 2004, 483, 317-322; al-Swayeh, O. A.; Futter, L. E.; Clifford, R. H.; Moore, P. K. Nitroparacetamol exhibits anti-inflammatory and anti-nociceptive activity. *Br. J. Pharmacol.*, 2000, 130, 1453-1456; AND, Paul Clark, M. J.; Howat, D.; Flower, R. J.; Moore, P. K.; Perretti, M. Nitroparacetamol (NCX-701) exhibits anti-inflammatory activity in the zymosan air pouch. *Inflamm. Res.*, 2001, 50, S158] demonstrating that NCX 701 is not only a safer drug than paracetamol, but that it also possesses a wider action due to additive mechanisms. Several papers have compared the antinociceptive activity of NCX 701 versus paracetamol, [Romero-Sandoval, E. A.; Mazario, J.; Howat, D.; Herrero, J. F. NCX-701 (nitroparacetamol) is an effective antinociceptive agent in rat withdrawal reflexes and wind-up. *Br. J. Pharmacol.*, 2002, 135, 1556-1562; Romero-Sandoval, A. E.; Del Soldato, P.; Herrero, J. F. The effects of sham and full spinalization on the antinociceptive effects of NCX-701 (nitroparacetamol) in monoarthritic rats. *Neuropharmacology*, 2003, 45, 412-419; and Gaitán, G.; Del Soldato, P.; Herrero, J. F. Low doses of nitroparacetamol or dexketoprofen trometamol enhance fentanyl antinociceptive activity.

*Eur. J. Pharmacol.*, 2003, 481, 181-188]. regularly showing the superiority of NCX 701. Moreover, sub-effective doses of NCX 701 have enhanced the anti-nociceptive activity of the μ-opioid receptor agonist fentanyl. A Phase II study clinical trial has demonstrated that 1 g NCX 701 provides similar analgesic efficacy to paracetamol 1 g in post-operative dental pain, therefore with a reduced exposure to paracetamol, confirming a contribution of NO to the anti-nociceptive mechanisms of NCX 701.

O-Dealkylation of a homologous series of alkoxy acetanilides [p-methoxy, p-ethoxy: phenacetin, p-(n)-propoxy- and p-(n)-butoxy acetanilides; 4-7] have shown to release paracetamol.

The compounds (6 and 7) were structurally related to phenacetin (5), and were synthesized to check whether they release paracetamol (1) upon O-dealkylation, which they did. The chain length in the synthesized compounds was varied to study the effect of chain lengthening on the rate of release of paracetamol.

[Chul-Ho, Y., Miller, G. P., Guengerich, F. P. Oxidations of p-Alkoxyacylanilides Catalyzed by Human Cytochrome P450 1A2: Structure-Activity Relationships and Simulation of Rate Constants of Individual Steps in Catalysist *Biochemistry* 2001, 40, 4521-4530]

The compounds (4, 6 and 7) are structurally related to phenacetin (5) therefore, on metabolism they will liberate paracetamol (1).

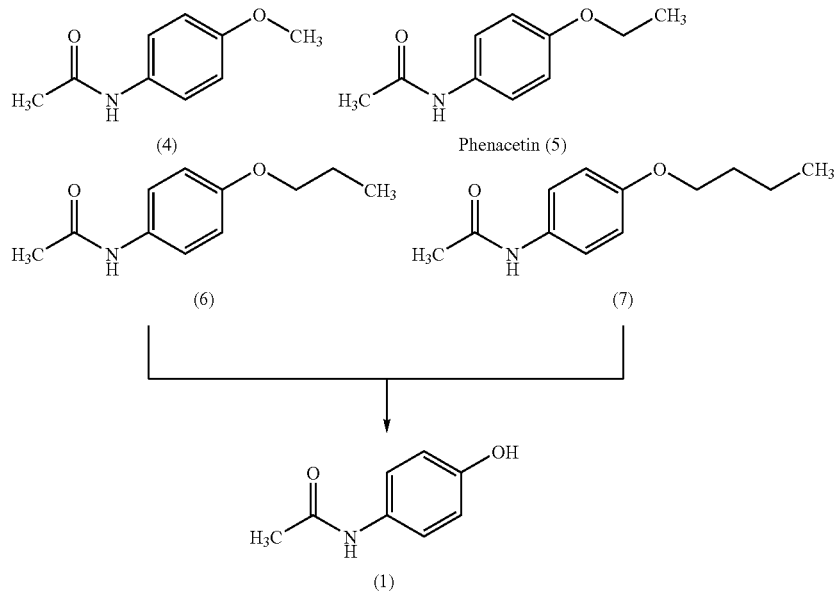

Release of Paracetamol (1) by Alkoxy Acetanilides (4-7)

There was a need to develop the novel molecules which are having better analgesic and anti-inflammatory activity. The advantages of the present invention are that these NO releasing compounds have shown better analgesic and anti-inflammatory activity than the parent drug, and less liver toxicity in biochemical and histopathological studies.

The present invention deals with ether derivatives of paracetamol, whereas the prior art has ester derivatives. The rate of release of NO will be different in both the compounds.

OBJECTS OF THE INVENTION

The main object of the present invention is to provide novel nitrate esters of paracetamol.

Another object of the present invention is to provide process for preparation of novel nitrate esters of paracetamol.

Yet another object of the present invention is to develop nitric oxide releasing derivative of paracetamol that shows better analgesic, anti-inflammatory, biochemical (SGOT, ALP levels) and histopathologic profile.

Further object of the present invention is to develop a pharmaceutical composition comprising nitric oxide releasing derivatives of paracetamol.

Still another object of the present invention is to inhibit COX-2 in vitro and release NO in vivo. Yet another object of the present invention is to develop a pharmaceutical composition that shows better COX-2 (in vitro) than the parent drug paracetamol.

In vivo nitric oxide release was studied and nitrate concentration (μmol/l) in control, (12) and (13) was found to be 182.1±0.68, 354.2±2.17 and 265.4±2.47 respectively.

Therefore, it can be concluded that the NO releasing compound is showing better activity than the parent drug candidate, and moreover, the biochemical and histopathological studies carried out, indicate that the compound is causing less liver toxicity than paracetamol.

Compound (13) has shown to have better COX-2 (in vitro) inhibition activity i.e. 32.5% than the parent drug paracetamol (1) which had 24.0%. The compounds 12 and 13 also released NO in vivo.

SUMMARY OF THE INVENTION

The present invention relates to the synthesis of NO-releasing derivatives of paracetamol and their evaluation. The compounds showed better analgesic, anti-inflammatory, biochemical and histopathologic profile. The present invention particularly relates to novel nitrate esters of paracetamol. The nitrate esters of paracetamol are prepared by reacting the paracetamol with dihaloalkyl compound and followed by reaction with silver nitrate to obtain the corresponding nitrate ester derivatives.

NO-releasing derivatives of paracetamol showed good anti-inflammatory activity (less in % increase in paw volume) with respect to parent drug Paracetamol, both at 2 hour and 4 hour interval. O-alkylated NO-releasing derivatives of Paracetamol exhibited better analgesic response than the parent drug indicated by greater percentage inhibition in writhings. The intermediates having terminal Br (which was later converted to —$ONO_2$ moiety on treatment with AgNO3) showed very negligible percentage Inhibition in writhings indicating that NO release is responsible for better analgesic activity of the compounds having NO releasing —ONO: moiety. In NO releasing activity also showed significant increase in level of NO. The NO release of these compounds could be the acting force behind their better analgesic and anti-inflammatory activities than the parent drug. The present compound has shown to have better COX-2 (in vitro) than the parent drug paracetamol. In the case of biochemical studies paracetamol caused a significant increase in the serum ALP levels as compared to the NO-releasing derivatives, indicating its liver toxicity. Both the derivatives were found to increase the levels of ALP but not more than the drug. Increase in the levels of SGPT (ALT) 6 hr after administration of paracetamol (1) justified its liver toxicity, with % increase more than 80%. Increase in the case of both the derivatives was not that significant. In histopathological studies, the damage caused by present No releasing compounds, to liver was less in comparison to Paracetamol. Therefore, the said compounds showed better activity and lesser toxicity than the parent drug.

10 and 11 are intermediates only which were later converted to —ONO, moiety on treatment with $AgNO_3$. The lesser % inhibition in writhings (in case of 10 and 11) indicates that NO release is responsible for better analgesic activity of the compounds 12 and 13 (having NO releasing —$ONO_2$ moiety).

Figure 2:
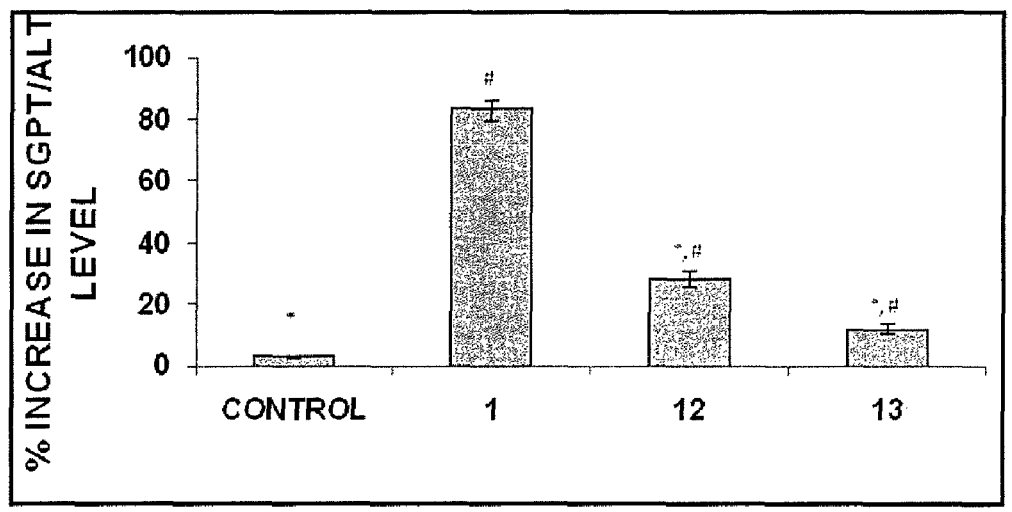

FIG. 2: % increase in SGOT levels after 6 hours

Figure 3:
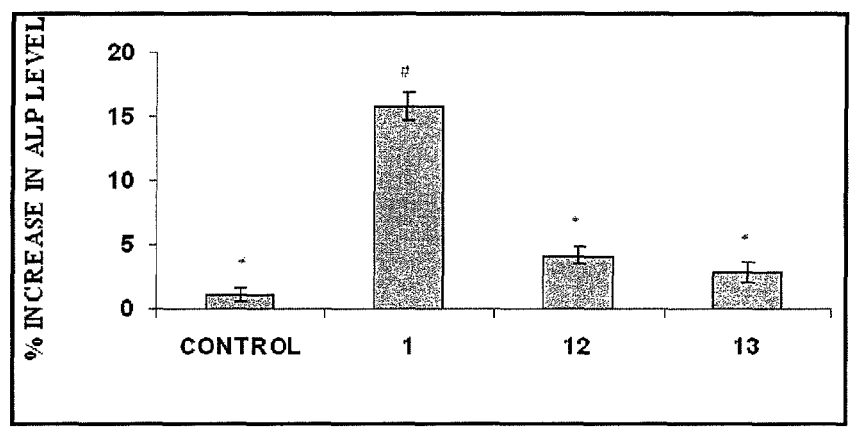

FIG. 3: % increase in ALP levels after 6 hours (Explanation for FIG. 2 and FIG. 3)

Overproduction of toxic metabolite 2 leads to depletion of glutathione stores in liver and further accumulation of the toxic metabolite causes tissue injury and cell death. Enzymes like alkaline phosphatase (ALP, EC 3.1.3.1), serum glutamate pyruvate transaminase (SGPT) or alanine aminotransferase (ALT) (EC 2.6.1.2) and the total proteins are considered as plasma markers of liver injury. Nitric oxide releasing paracetamol derivatives (12 and 13) were evaluated for their effect on the markers of liver injury like enzymes ALP and SGPT/ALT. The plasma levels of these enzymes were found to increase in the case of liver toxicity. The graph indicates that the rise (with comparison to the basal value) in the case of 1 is much more than in the case of NO releasing derivatives (12 and 13), showing that they cause lesser liver toxicity than the parent drug Paracetamol (1).

Percentage increase SGGT/ALT and ALP enzymes are direct indication of liver toxicity as explained in the above paragraph. FIGS. 2 and 3 are self explanatory as percentage. increase in both the enzyme levels after administration of Paracetamol which is a proven liver toxic have been found to be greater in comparison to 12 and 13. The nitric oxide released by the compounds 12 and 13 must have played a protective role in liver protection and thereby percentage increase in SGPT/ALT and ALP levels has been significantly low in comparison to the parent drug Paracetamol.

Figure 4:
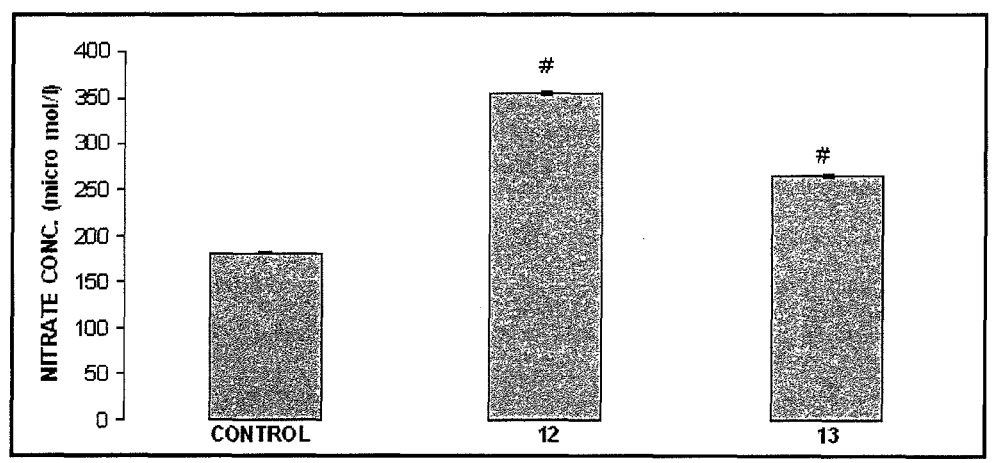

FIG. 4: Nitrate ion concentration (μmol/L) in serum after 6 hours

The graph indicates that the serum NO concentration 6 hours after administration of 12 and 13 was greater than the control (0.9% w/v sodium chloride containing 20% v/v tween-80) confirming that these compounds release NO in vivo.

The nitrate concentration (μmol/L), 6 hours after administration in control (no derivative administered), 12 and 13 was found to be 182.1±0.68, 354.2±2.17 and 265.4±2.47 respectively, indicating that 12 and 13 releases NO in vivo.

Figure 5:
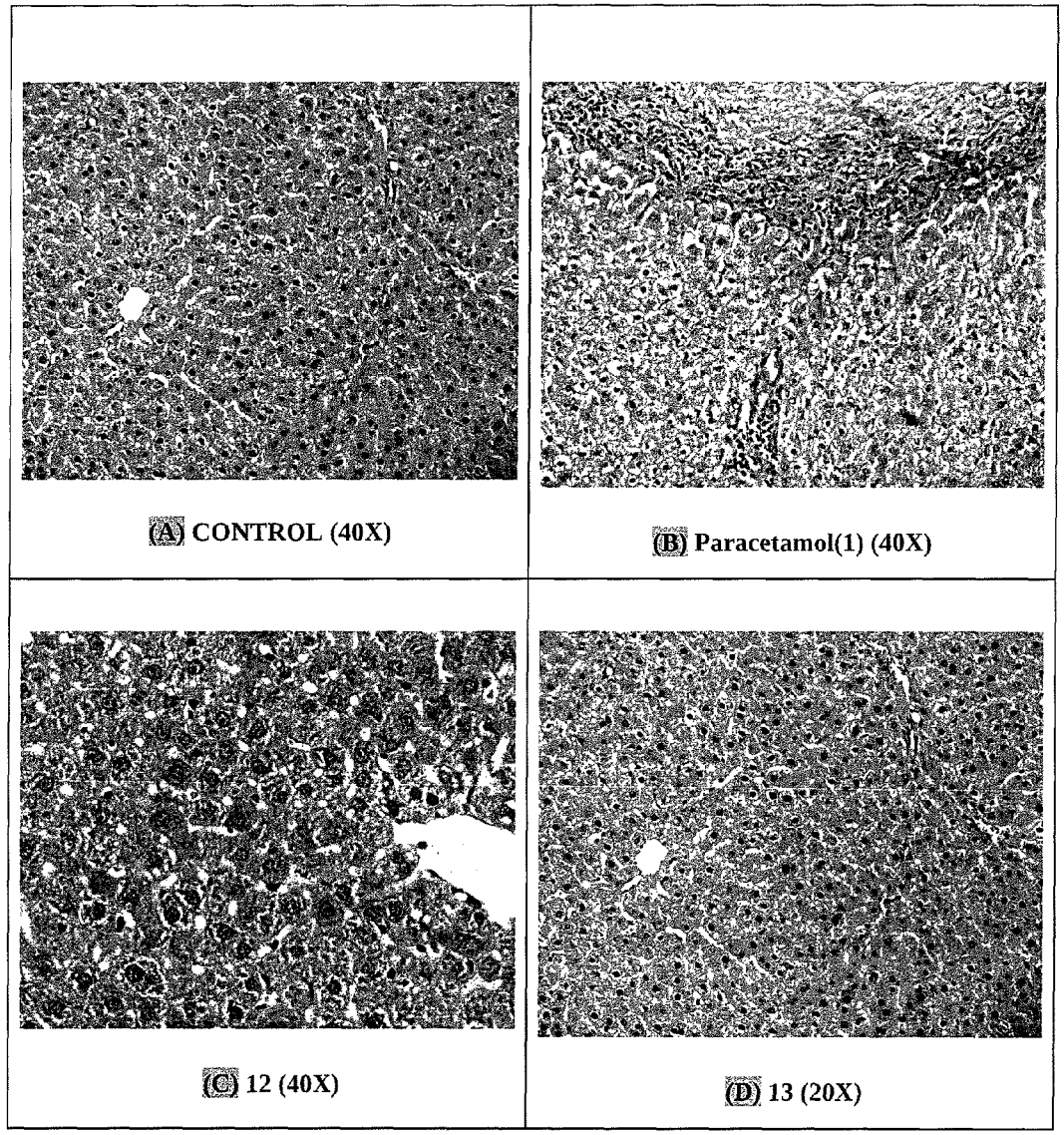

FIG. 5: Histopathology (haematoxylin and eosin) of liver samples

Light microscopic analysis of liver samples obtained from mouse treated with control (0.9% w/v sodium chloride containing 20% v/v tween-80), Paracetamol (1), (12) and (13), at a dose of 1000 mg/kg, intra peritoneal is shown in sections (A), (B), (C), and (D), respectively. The interpreted results obtained from histopathological studies are summarized below:

(i) Control did not cause any damage to the liver. Only mild portal triad inflammation was observed.

(ii) Paracetamol (1) a proven liver toxic caused ballooning degeneration, sinusoidal decongestion, portal triad inflammation and spoty necrosis in Zone I.

(iii) Just mild ballooning degeneration was observed in the case of 12.

(iv) Compound 13 also didn't cause any significant damage to the liver.

These results were supportive in summarizing that NO-release counteracts the liver toxic side effects of Paracetamol (1).

The details have been explained in the above paragraph. Only Paracetamol (1) caused liver toxicity indicated by ballooning degeneration, sinusoidal decongestion, portal triad inflammation and spoty necrosis in Zone I in histopathology. Only mild portal triad inflammation was observed in case of control, Mild ballooning degeneration in case of 12 and no significant damage in 13, showing the liver protective effect of the synthesized derivatives 12 and 13 due to their NO release.

DETAILED DESCRIPTION OF THE INVENTION

Accordingly the present invention provides nitrate ester derivatives of paracetamol of general formula A, wherein the value of n is selected from 2 to 5.

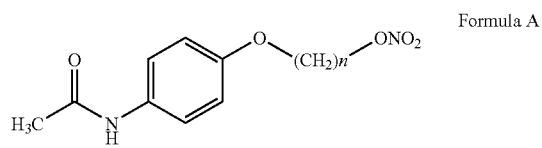

Formula A

In an embodiment of the invention wherein the structural formula A comprising

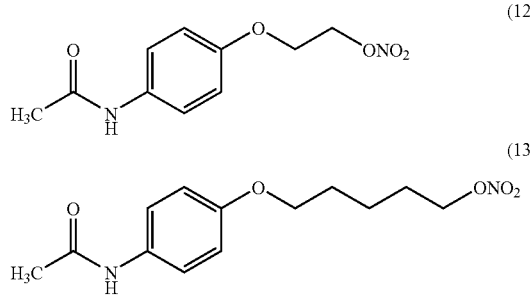

(12)

(13)

In an embodiment of the invention wherein the representative compounds of the general formula A comprising:
(i) N-[4-(2-Nitrooxy-ethoxy)-phenyl]-acetamide (12)
(ii) N-[4-(5-Nitrooxy-pentoxy)-phenyl]-acetamide (13)
(iii) N-[4-(3-Nitrooxy-propoxy)-phenyl]-acetamide (18)
(iv) N-{4-(4-Nitrooxy-butoxy)-phenyl}-acetamide (19)

In another embodiment of the invention wherein the compound of formula A is having better peripheral analgesic activity and significant anti-inflammatory activity as compared to paracetamol.

In yet another embodiment of the invention wherein the compounds possess better analgesic and antiinflamatory activity and devoid of toxicity as compared to the parent drug paracetamol (1).

In still another embodiment of the invention wherein the compounds 12 and 13 showed 32.68±1.45% and 31.15±1.31% at 2 hr, and, 26.44±0.10% and 28.45±1.28% at 4 hr increase respectively, in the paw volume as compared to 38.37±1.26% and 58.92±1.56% (at 2 hr and 4 hr respectively) in case of paracetamol at a dose of 100 mg/kg body weight.

In a further embodiment of the invention wherein the compounds 12 and 13 showed increase in NO serum level 354.2±2.17 and 265.4±2.47 respectively w.r.t. control (182.1±0.68) at a dose of 100 mg/kg body weight.

In an embodiment of the invention wherein the compound 13 showed in vitro cox-2 (ovine) inhibitory activity 32.5% as compared to control 24.0%.

Accordingly the present invention provides a process for preparation of nitrate ester derivative of paracetamol comprising the steps:
a) reacting paracetamol with dibromo alkane in organic solvent in presence of alkali carbonate for a period up to 12 hours,
b) filtering the reaction mixture followed by evaporation of solvent to obtain solid residue,
c) dissolving the residue in water immisible solvent and washing with sodium hydroxide solution followed by washing with water, evaporating the solvent to O-alkylated bromo derivative of paracetamol,
d) reacting the O-alkylated bromo derivative of paracetamol with sliver nitrate under reflux in an aprotic solvent up to 12 hours, further filtering and evaporating the filterate to obtain the nitrate esters derivative of Paracetamol of general formula A wherein the value of n is selected from 2-5.

In an embodiment of the invention wherein dihalo alkane may be selected from a group consisting of 1,2-dibromoethane, 1,3-dibromopropane, 1,4-dibromobutane and 1,5-dibromopentane.

In an embodiment of the invention wherein the organic solvent used may be selected from a group consisting of ethyl methyl ketone, acetone, acetonitrile and mixture thereof.

In an embodiment of the invention wherein the aprotic solvent used may be selected from a group consisting of acetonitrile, benzene, hexane and mixture thereof.

The pharmaceutical composition may be prepared using the compounds of the general formula A along with the pharmaceutically acceptable excipients.

Compounds 12 and 13 are novel and have not been reported earlier. Compound (13) has shown to have better COX-2 inhibition activity (in vitro) than the parent drug paracetamol. The data of analgesic and anti-inflammatory activities is exactly complimenting and supporting it. Therefore, it can be concluded that the NO releasing compound is showing better activity than the parent drug candidate, and moreover, the biochemical and histopathological studies carried out, indicate that the compound is causing less liver toxicity than paracetamol.

NO-releasing derivatives of paracetamol, (12) and (13) showed good anti-inflammatory activity w.r.t. parent drug, both at 2 hr and 4 hr interval. No significant activity was observed in case of paracetamol (1). O-alkylated NO-releasing derivatives (12 and 13) of paracetamol (1) exhibited better response than the parent drug indicated by greater % inhibition in writings. The intermediates 10 and 11, having terminal Br (which was later converted to —$ONO_2$ moiety on treatment with $AgNO_3$) showed very negligible % inhibition in writings indicating that NO release is responsible for better analgesic activity of the compounds 12 and 13 (having NO releasing —$ONO_2$) moiety. In NO releasing activity they also showed significant increase in level of NO. The NO release of these compounds could be the acting force behind their better analgesic and anti-inflammatory activities than the parent drug. Our compound (13) has shown to have better COX-2 (in vitro) than the parent drug paracetamol. In the case of biochemical studies paracetamol (1) caused a significant increase in the serum ALP levels as compared to the NO-releasing derivatives (12 and 13), indicating its liver toxicity. Both the derivatives were found to increase the levels of ALP but not more than the drug. Increase in the levels of SGPT (ALT) 6 hr after administration of paracetamol (1) justified its liver toxicity, with % increase more than 80%. Increase in the case of both the derivatives (12 and 13) was not that significant. In histopathological studies, also the damage caused by 12 and 13, to liver was less in comparison to paracetamol (1). Therefore, compounds 12 and 13 showed better activity and lesser, toxicity than the parent drug 1.

Paracetamol (1), a proven liver toxic and having no anti-inflammatory activity of its own has been converted to more active and lesser toxic NO releasing compounds 12 and 13.

Nitric oxide releasing derivatives of paracetamol are developed (12 and 13) (FIG. 2), which have shown better analgesic, anti-inflammatory, biochemical (SGOT, ALP levels) and histopathologic profile. Besides these derivatives have shown to inhibit COX-2 in vitro and release NO in vivo.

Problem: Paracetamol (1), a proven liver toxic and having no anti-inflammatory activity of its own. The present invention is successful in converting it to more active (better analgesic and anti-inflammatory activity) and lesser liver toxic drivatives.

The liver toxic drug paracetamol (1) having no anti-inflammatory activity has been converted to less liver toxic and more active derivatives. Briefly, Paracetamol was stirred in a solution of 1,2-dibromoethane (8) and 1,5-dibromopentane (9), in ethyl methyl ketone and $K_2CO_3$ for 8-10 hours.

The resulting solution was filtered, dried and evaporated to get a solid residue. The residue was dissolved in CHCl$_3$ and washed with 5% NaOH (3×100 ml) and water (3×100 ml), dried over anhydrous Na$_2$SO$_4$, filtered and solution evaporated to get O-alkyl derivatives 10 and 11, respectively. These were refluxed in a solution of AgNO$_3$ and acetonitrile overnight, filtered, and evaporated to get nitrate esters 12 and 13, respectively.

$^{13}$C NMR (CDCl$_3$): δ 23.49 (—NHCOCH$_3$), 29.03 (—CH$_2$Br—), 67.66 (—OCH$_2$—), 114.40 (2×2° Ar—C), 121.06 (2×2° Ar—C), 132.20 (1×3° Ar—C), 153.72 (1×3° Ar—C) and 168.26 (—NHCOCH$_3$)

Calcd. for C$_{10}$H$_{12}$BrNO$_2$: C, 46.53; H, 4.69; N, 5.43. Found: C, 46.77; H, 4.17; N, 5.24.

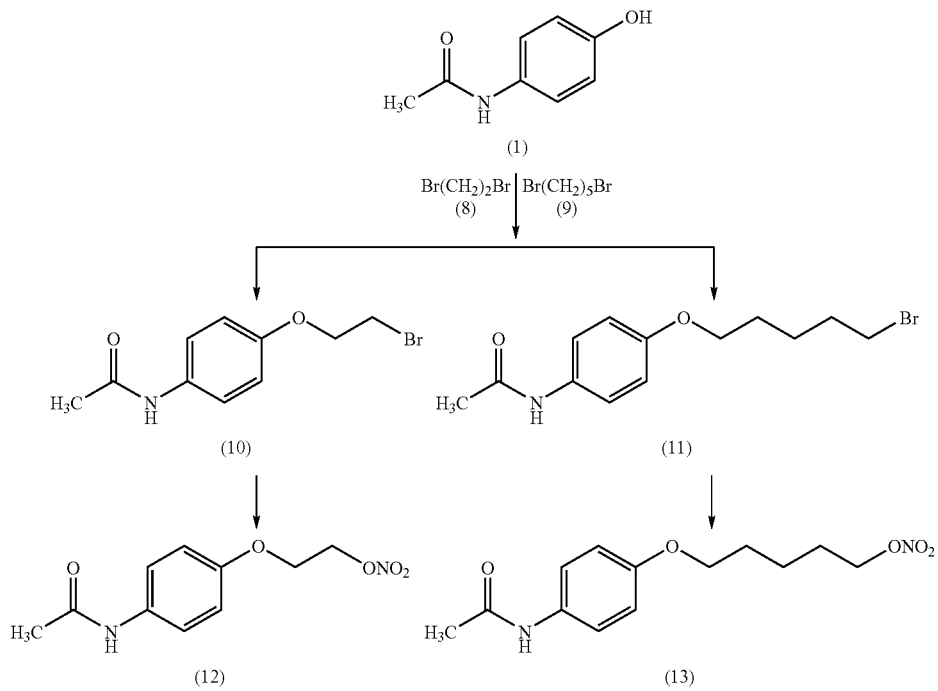

Synthesis of No Releasing Derivatives (12 and 13) of Paracetamol (1)

Following examples are given by way of illustration and should not construed to limit the scope of the invention

EXAMPLE 1

N-[4-(2-Bromo-ethoxy)-phenyl]-acetamide (10)

A solution of N-(4-hydroxyphenyl)-acetamide (paracetamol) (1) (1.50 g, 0.01 mol) and 1,2-dibromoethane (8) (10.0 ml) in ethyl methyl ketone (25.0 ml) containing potassium carbonate (5.0 g) was stirred for 8 hr at room temperature. The reaction mixture was filtered, residue washed with ethyl methyl ketone and solvent evaporated under reduced pressure to get the residue. The residue was dissolved in chloroform (200.0 ml), washed with 5% NaOH solution (3×100 ml), water (3×50 ml), dried, filtered and crystallized from methanol to get the desired product N-[4-(2-bromo-ethoxy)-phenyl]-acetamide (10) (2.01 g, 78.51%), mp 126-127° C.

Analysis:

IR (KBr): 3302, 3024, 1662, 1551, 1242, 1029 and 828 cm$^{-1}$ $^1$H NMR (CDCl$_3$): δ 2.10 (s, 3H, —NHCOCH$_3$), 3.65 (t, 2H, J=5.9 Hz, CH$_2$Br), 4.26 (t, 2H, J=5.9 Hz, —OCH$_2$), 6.83 (d, 2H, Ar—H), 7.49 (d, 2H, Ar—H), 9.42 (s, 1H, —NH, Exchangeable with D$_2$O)

N-[4-(2-Nitrooxy-ethoxy)-phenyl]-acetamide (12)

A mixture of N-[4-(2-bromo-ethoxy)-phenyl]-acetamide (10) (1.30 g, 0.005 mol), silver nitrate (5.0 g) and freshly distilled acetonitrile (50.0 ml) was refluxed for 10 hr, cooled, poured into crushed ice and extracted with chloroform (3×100 ml). The combined organic layers were dried, filtered, solvent removed under reduced pressure to obtain a residue which was crystallized from methanol to obtain N-[4-(2-nitrooxy-ethoxy)-phenyl]-acetamide (12) (0.91 g, 75.83%), mp 106-107° C.

Anal.

IR (KBr): 3324, 3060, 2920, 1667, 1634, 1522, 1238, 1046 and 861 cm$^{-1}$ $^1$H NMR (CDCl$_3$): δ 2.15 (s, 3H, —NHCOCH$_3$), 4.21 (t, 2H, J=4.6 Hz, —OCH$_2$—), 4.80 (t, 2H, J=4.6 Hz, —CH$_2$ONO$_2$), 6.83 (d, 2H, Ar—H), 7.49 (d, 2H, Ar—H) and 7.43 (s, 1H, —NH, Exchangeable with D$_2$O)

$^{13}$C NMR (CDCl$_3$): δ 24.32 (—NHCOCH$_3$), 64.46 (—CH$_2$ONO$_2$—), 71.09 (—OCH$_2$—), 115.00 (2×2° Ar—C), 122.02 (2×2° Ar—C), 132.03 (1×3° Ar—C), 154.74 (1×3° Ar—C) and 168.62 (—NHCOCH$_3$)

Calcd. for C$_{10}$H$_{12}$N$_2$O$_5$: C, 50.00; H, 5.04; N, 11.66. Found: C, 49.76; H, 4.60; N, 11.19.

EXAMPLE 2

N-[4-(5-Bromo-pentoxy)-phenyl]-acetamide (11)

A solution of N-(4-hydroxyphenyl)-acetamide (paracetamol) (1) (1.50 g, 0.01 mol) and 1,5-dibromopentane (9) (10.0 ml) in ethyl methyl ketone (25.0 ml) containing potassium carbonate (5.0 g) was stirred for 8 hr at room temperature. The reaction mixture was filtered, residue washed with ethyl methyl ketone and solvent evaporated under reduced pressure to get the residue. The residue was dissolved in chloroform (200.0 ml), washed with 5% sodium hydroxide solution (3×100 ml), water (3×50 ml), dried, filtered and crystallized from methanol to get the desired product N-[4-(5-bromo-pentoxy)-phenyl]-acetamide (11) (2.15 g, 72.15%), mp 110-111° C.

Anal.

IR (KBr): 3303, 3031, 2944, 1660, 1549, 1410, 1239, 1045 and 735 cm$^{-1}$ $^1$H NMR (CDCl$_3$): δ 1.62 (m, 2H, —CH$_2$CH$_2$CH$_2$—), 1.81 (p, 2H, J=7.4 Hz, —OCH$_2$CH$_2$—), 1.92 (m, 2H, —CH$_2$CH$_2$Br—), 2.11 (s, 3H, —NHCOCH$_3$), 3.43 (t, 2H, J=6.3 Hz, —CH$_2$Br), 3.92 (t, 2H, J=6.3 Hz, —OCH$_2$—), 6.81 (d, 2H, Ar—H), 7.37 (d, 2H, Ar—H) and 9.42 (s, 1H, —NH, Exchangeable with D$_2$O)

$^{13}$C NMR (CDCl$_3$): δ 24.20 (—NHCOCH$_3$), 24.83 (—CH$_2$CH$_2$CH$_2$—), 28.45 (—OCH$_2$CH$_2$—), 32.49 (—CH$_2$CH$_2$Br—), 33.68 (—CH$_2$Br—), 67.87 (—OCH$_2$—), 114.72 (2×2° Ar—C), 122.06 (2×2° Ar—C), 131.05 (1×3° Ar—C), 155.84 (1×3° Ar—C) and 168.70 (—NHCOCH$_3$)

Calcd. for C$_{13}$H$_{18}$BrNO$_2$: C, 52.01; H, 6.04; N, 4.67. Found: C, 52.67; H, 5.54; N, 4.74.

N-[4-(5-Nitrooxy-pentoxy)-phenyl]-acetamide (13)

A mixture of N-[4-(5-bromo-pentoxy)-phenyl]-acetamide (11) (1.50 g, 0.005 mol)), silver nitrate (5.0 g) and freshly distilled acetonitrile (50.0 ml) was refluxed for 10 hr, cooled, poured into crushed ice and extracted with chloroform (3×100 ml). The combined organic layers were dried, filtered, solvent removed under reduced pressure to obtain a residue which was crystallized from methanol to obtain N-[4-(5-nitro oxy-pentoxy)-phenyl]-acetamide (13) (1.02 g, 72.34%), mp 96-98° C.

Anal.

IR (KBr): 3322, 3025, 2951, 1663, 1547, 1236, 1048, 878 and 739 cm$^{-1}$ $^1$H NMR (CDCl$_3$): δ 1.59 (m, 2H, —CH$_2$CH$_2$CH$_2$—), 1.84 (m, 4H, —CH$_2$CH$_2$CH$_2$—), 2.10 (s, 3H, —NHCOCH$_3$), 3.93 (t, 2H, J=6.6 Hz, —OCH$_2$—), 4.49 (t, 2H, J=6.6 Hz, —CH$_2$ONO$_2$), 6.80 (d, 2H, Ar—H), 7.45 (d, 21-1, Ar—H), 9.10 (s, 1H, —NH, Exchangeable with D$_2$O)

$^{13}$C NMR (CDCl$_3$): δ 22.52 (—NHCOCH$_3$), 24.36 (—CH$_2$CH$_2$CH$_2$—), 26.64 (—OCH$_2$CH$_2$—), 28.83 (—CH$_2$CH$_2$ONO$_2$—), 67.74 (—CH$_2$ONO$_2$—), 73.23 (—OCH$_2$—), 114.80 (2×2° Ar—C), 122.01 (2×2° Ar—C), 131.11 (1×3° Ar—C), 155.83 (1×3° Ar—C) and 168.40 (—NHCOCH$_3$)

Calcd. for C$_{13}$H$_{18}$N$_2$O$_5$: C, 55.31; H, 6.43; N, 9.92. Found: C, 54.89; H, 6.19; N, 9.47.

Compounds 10 and 11 are the intermediates and are synthesized as per literature references:

(10): A Multi-Mode-Driven Molecular Shuttle: Photochemically and Thermally Reactive Azobenzene Rotaxanes. Murakami, Hiroto; Kawabuchi, Atsushi; Matsumoto, Rika; Ido, Takeshi; Nakashima, Naotoshi. Department of Applied Chemistry, Faculty of Engineering, Nagasaki University, Nagasaki, Japan. Journal of the American Chemical Society (2005), 127(45), 15891-15899.

(11): Antagonists of slow reacting substance of anaphylaxis. Synthesis of a series of chromone-2-carboxylic acids. Appleton, R. A.; Bantick, J. R.; Chamberlain, T. R.; Hardem, D. N.; Lee, T. B.; Pratt, A. D. Pharm. Div., Fisons Ltd., Loughborough/Leicestershire, UK. Journal of Medicinal Chemistry (1977), 20(3), 371-9.

Examples of compounds with C3 and C4 chains are given below;

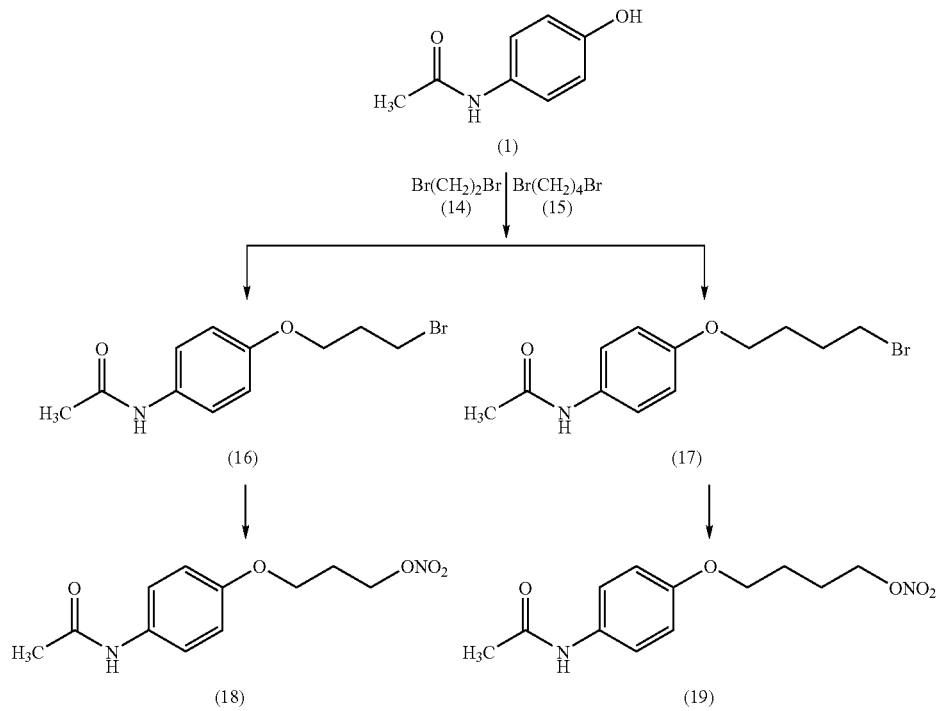

EXAMPLE 3

N-[4-(3-Bromo-propoxy)-phenyl]-acetamide (16)

A solution of N-(4-hydroxyphenyl)acetamide (paracetamol) (1) (1.50 g) and 1,3-dibromobutane (14) (10.0 ml) in ethyl methyl ketone (25.0 ml) containing potassium carbonate (5.0 g) was stirred overnight at room temperature. The reaction mixture was filtered, residue washed with ethyl methyl ketone and solvent evaporated under reduced pressure to get the residue. The residue was dissolved in chloroform (200.0 ml), washed with 5% NaOH solution (3×100 ml), water (3×50 ml), dried, filtered and crystallized from methanol to get the desired product N-[4-(3-Bromo-propoxy)-phenyl]-acetamide (16) (2.01 g, 75.8%), mp 115-118° C.

Analysis:

IR (KBr): 3284, 1658, 1559, 1410, 1239, 1032, 832 and 521 cm$^{-1}$ $^1$H NMR (400 MHz, CDCl$_3$): δ 2.14 (s, 3H, —NHCOCH$_3$), δ 2.30 (p, 2H, J=6.1, —CH$_2$CH$_2$Br—), δ 3.59 (t, 2H, J=6.4 Hz, —CH$_2$Br), δ 4.07 (t, 2H, J=5.8 Hz, —OCH$_2$—): δ 6.86 (d, 2H, J=3.0 Hz, Ar—H), δ 7.37 (d, 2H, J=3.0 Hz, Ar—H) and δ 7.27 (s, 1H, —NH, Exchangeable with D$_2$O)

$^{13}$C NMR (400 MHz, CDCl$_3$): δ 24.40 (—NHCOCH$_3$), δ 30.14 (—CH$_2$CH$_2$CH$_2$Br—), δ 32.36 (—CH$_2$Br—), δ 65.58 (—OCH$_2$—), δ 114.84 (2×2° Ar—C), δ 122 (2×2° Ar—C), δ 131.23 (1×3° Ar—C), δ 155.55 (1×3° Ar—C) and δ 168.43 (—NHCOCH$_3$)

CHN: Calculated: C, 48.55; H, 5.19; N, 5.15. Found: C, 48.76; H, 5.10; N, 4.36.

N-[4-(3-Nitrooxy-propoxy)-phenyl]-acetamide (18)

A mixture of N-[4-(3-Bromo-propoxy)-phenyl]-acetamide (16) (1.50 g), silver nitrare (5.0 g) and freshly distilled acetonitrile (50.0 ml) was refluxed for 10 hr, cooled, poured into crushed ice and extracted with chloroform (3×100 ml). The combined organic layers were dried, filtered, solvent removed under reduced pressure to obtain a residue which was crystallized from methanol to obtain N-[4-(3-Nitro oxy-propoxy)-phenyl]acetamide (18) (1.09 g, 77.30%), mp 89-92° C.

Analysis

IR (KBr: 3333, 1664, 1548, 1411, 1238, 1057, 839 and 704 cm$^{-1}$ $^1$H NMR (400 MHz, CDCl$_3$): δ 2.14 (s, 3H, —NHCOCH$_3$), δ 2.19 (p, 2H, J=6.1 —CH$_2$CH$_2$CH$_2$—), δ 4.66 (t, 2H, J=6.3 Hz, —OCH$_2$—), δ 4.03 (t, 2H, J=5.9 Hz, —CH$_2$ONO$_2$), δ 6.84 (d, 2H, J=3.1 Hz, Ar—H), δ 7.41 (d, 2H, J=3.8 Hz, Ar—H) and δ 7.26 (s, 1H, —NH, Exchangeable with D$_2$O)

$^{13}$C NMR (400 MHz, CDCl$_3$): δ 24.40 (—NHCOCH$_3$), δ 27.0 (—CH$_2$CH$_2$CH$_2$—), δ 63.80 (—CH$_2$ONO$_2$—), δ 70.00 (—OCH$_2$), δ 77.11 (—OCH$_2$—), δ 114.76 (2×2° Ar—C), δ 121.98 (2×2° Ar—C), δ 131.46 (1×3° Ar—C), δ 155.27 (1×3° Ar—C) and δ 168.46 (—NHCOCH$_3$)

CHN: Calculated: C, 51.97; H, 5.55; N, 11.02. Found: C, 48.63; H, 5.37; N, 10.79.

EXAMPLE 4

N-[4-(4-Bromo-butoxy)-phenyl]-acetamide (17)

A solution of N-(4-hydroxyphenyl)acetamide (Paracetamol) (1) (1.50 g) and 1,3-dibromobutane (15) (10.0 ml) in acetonitrile (25.0 ml) containing potassium carbonate (5.0 g) was refluxed for 8 hrs. at room temperature. The reaction mixture was filtered and the filtrate was poured into ice cold water. The residue was filtered and washed with 5% NaOH solution (3×100 ml), water (3×50 ml), dried, filtered and crystallized from methanol to get the desired product N-[4-(4-bromobutoxy)phenyl]acetamide (17) (2.15 g, 77.06), mp 119-124° C.

Analysis:

IR (KBr): 3289, 1660, 1552, 1409, 1236, 1046, 825 and 520 cm$^{-1}$ $^1$H NMR (400 MHz, CDCl$_3$): δ 2.04 (s, 3H, —NHCOCH$_3$), δ 2.06 (p, 2H, J=2.13 Hz, (—CH$_2$CH$_2$CH$_2$Br), δ 1.94 (p, 2H, J=3.35 Hz, (—CH$_2$CH$_2$CH$_2$CH$_2$Br), δ 3.48 (t, 2H, J=6.6 Hz, CH$_2$Br), δ 3.98 (t, 2H, J=6.0 Hz, —O—(CH$_2$), δ 6.85 (d, 2H, J=3.0 Hz, Ar—H), δ 7.37 (d, 2H, J=3.0 Hz, Ar—H), δ 7.26 (s, 1H, —NH, Exchangeable with D$_2$O)

$^{13}$C NMR (400 MHz, CDCl$_3$): δ 24.38 (—NHCOCH$_3$), δ 27.91 (—CH$_2$CH$_2$CH$_2$Br), δ 29.48 (—CH$_2$CH$_2$CH$_2$Br), δ 33.60 (—CH$_2$Br—), δ 67.10 (—OCH$_2$—), δ 114.72 (2×2° Ar—C), δ 121.99 (2×2° Ar—C), δ 131.07 (1×3° Ar—C), δ 155.72 (1×3° Ar—C) and δ168.46 (—NHCOCH$_3$)

CHN: Calculated: C, 50.37; H, 5.64; N, 4.89. Found: C, 49.96; H, 5.73; N, 4.68.

N-[4-(4-Nitro oxy-butoxy)-phenyl]-acetamide (19)

A mixture of N-[4-(4-bromobutoxy)phenyl]acetamide (17) (1.30 g), silver nitrare (5.0 g) and freshly distilled acetonitrile (50.0 ml) was refluxed for 10 hr, cooled, poured into crushed ice and extracted with chloroform (3×100 ml). The combined organic layers were dried, filtered, solvent removed under reduced pressure to obtain a residue which was crystallized from methanol to obtain N-[4-(4-Nitro oxy-butoxy)-phenyl]-acetamide (19) (1.10 g, 78%), mp 92-98° C.

Analysis:

IR (KBr): 3327, 1658, 1519, 1408, 1238, 1040, 832 and 551 cm$^{-1}$ $^1$H NMR (400 MHz, CDCl$_3$): δ 2.07 (s, 3H, —NHCOCH$_3$), δ 1.88 (p, 2H, J=2.7 Hz, —CH$_2$CH$_2$CH$_2$CH$_2$ONO$_2$), δ 1.79 (p, 2H, J=2.9 Hz, —CH$_2$CH$_2$CH$_2$ONO$_2$), δ 3.91 (t, 2H, J=5.68 Hz, —CH$_2$ONO$_2$), δ 4.46 (t, 2H, J=6.2 Hz, —OCH$_2$—), δ 6.76 (d, 2H, J=3.09 Hz, Ar—H), δ 7.32 (d, 2H, J=3.09 Hz, Ar—H) and δ 7.30 (s, 1H, —NH, Exchangeable with D$_2$O)

$^{13}$C NMR (30 MHz, CDCl$_3$): δ 23.89 (—NHCOCH$_3$), δ 25.60 (—CH$_2$CH$_2$CH$_2$ONO$_2$), δ 24.43 (—CH$_2$CH$_2$CH$_2$ONO$_2$), δ 67.22 (—CH$_2$ONO$_2$—), δ 73.02 (—OCH$_2$—), δ 114.75 (2×2° Ar—C), δ 121.99 (2×2° Ar—C), 131.16 (1×3° Ar—C), δ 155.61 (1×3° Ar—C) and δ 168.36 (—NHCOCH$_3$)

CHN: Calculated: C, 53.73; H, 6.01; N, 10.44. Found: C, 52.94; H, 6.01; N, 9.90.

Biological Activity:

Animals: Wistar rats (male 150-200 g) of both sex and Laca mice (male, 25-35 g) procured from Central Animal House, Punjab University, Chandigarh, India were used. Animals were housed under standard laboratory conditions and maintained on rat chow, Animals were allowed free access to food and water until used and fasted 24 hr prior to studies.

Experimental conditions: Unless otherwise stated, the following conditions were employed in all experiments. The test compounds were suspended in 0.5% carboxymethylcellulose (CMC) and administered per orally (p.o.). Control animals were given the corresponding amount of vehicle (0.5%, CMC).

Anti-inflammatory activity (Table 1): Anti-inflammatory activity was determined by using carrageenan induced rat paw edema model. Rats were divided into different groups and the drugs were administered to each group.

Paw edema in rats (various modifications and various irritants) is the most widely used method for testing acute and subacute inflammation. It is based upon the ability of anti-inflammatory agents to inhibit the edema produced in the hind paw of the rat after injection of a phlogistic agent. Many phlogistic agents (irritants) have been used, such as brewer's yeast, formaldehyde, dextran, egg albumin, kaolin, sulfated polysaccharides like carrageenin or naphthoylheparamine. The volume of the injected paw is measured before and after application of the irritant and the paw volume of the treated animals is compared to the control. The details of the experiment carried out are described below:

The paracetamol (1) and synthesized NO-releasing derivatives (12 and 13) were administered p.o. at a dose of 100 mg/kg, p.o., emulsified in 0.5% sodium carboxy methyl cellulose (0.5% sodium CMC). Anti-inflammatory activity was determined by using carrageenan induced rat paw edema model. Rats were divided into different groups and the drugs/derivatives were administered to each group. Acute edema was induced in left hind paw of rats by injecting freshly prepared solution of carrageenan (Type IV, 0.1 ml, 1%) under plantar region of left hind paw. In the right paw, saline (1 ml, 0.9%) was injected, which served as control for comparison. The increase in paw volume was measured by using plethysmometer (water displacement, UGO BASILE, Varese, Italy) at 2 hr and 4 hr after carrageenan challenge. Percentage change (increase) in paw volume was calculated and expressed as the amount of inflammation.

$$\% \text{ increase in paw volume at any time} = (V_1 - V_r)/V_r \times 100$$

Where, $V_1$ Volume of left paw
$V_r$=Volume of right paw (control)

TABLE 1

Anti-inflammatory activity of paracetamol (1) and NO-NSAIDs (12 and 13)

| Compound | dose (mg/kg, p.o.) | % Increase in paw volume Mean ± SEM | |
|---|---|---|---|
| | | 2 hr | 4 hr |
| Control | 0.5% CMC | 41.96 ± 1.71 | 65.17 ± 1.55 |
| 1 | 100.0 | 38.37 ± 1.26 | 58.92 ± 1.56 |
| 12 | 100 | 32.68 ± 1.45 | 26.44 ± .10 |
| 13 | 100 | 31.15 ± 1.31 | 28.45 ± 1.28 |

Results are expressed as mean ± standard error of mean (SEM).
* indicates P < 0.05 w.r.t. control (0.5% sodium CMC); and
# indicates P < 0.05 w.r.t. paracetamol (100 mg/kg p.o.)

NO-releasing derivatives of paracetamol (1), 12 and 13 showed good anti-inflammatory activity w.r.t. parent drug 1, both at 2 hr and 4 hr interval (shown by less % increase in paw volume). At 2 hr % increase in paw volume for 12 and 13 was 32.68±1.45 and 31.15±1.31 respectively, and at 4 hr % increase in paw volume for 12 and 13 was 26.44±0.10 and 28.45±11.28 respectively. No significant activity was observed in case of paracetamol (1) as % increase in paw volume at 2 hr and 4 hr was found to be 38.37±1.26 and 58.92±1.56 respectively.

Figure 1:
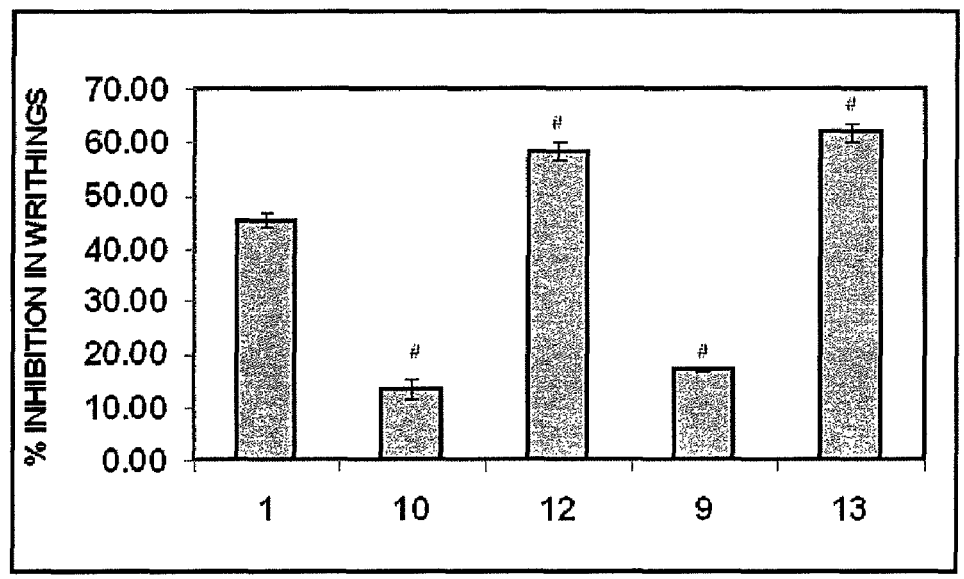
FIG. 1: Analgesic activity of paracetamol (1) and NO-NSAIDs (12 and 13)

Analgesic activity (Table 2 and FIG. 1 Sheet No. 1 FIG. 3): Analgesic activity was determined by using abdominal writhing assay. Mice were divided into different groups containing 6 animals in each group.

Pain can be induced by injection of irritants into the peritoneal cavity of mice. The animals react with a characteristic stretching behaviour which is called writhing. An irritating agent such as phenylquinone or acetic acid can be injected intraperitoneally to mice and the stretching reaction is evaluated. The most commonly used methods for measuring peripheral analgesic activity are the writhing tests in mice. The details of the experiment carried out are mentioned below:

Analgesic activity was determined against acetic acid induced writhing assay. Writhing was induced by intraperitoneal (i.p.) injection of freshly prepared acetic acid solution. Mice were per orally (p.o.) administered paracetamol (1) and synthesized NO-releasing derivatives (12 and 13) at a dose of 100 mg/kg, emulsified in 0.5% sodium carboxy methyl cellulose (sodium CMC) vehicle, 30 min prior to i.p. acetic acid (1% w/v in saline pH 2.7, 10 ml/kg, i.p.). Animals were immediately transferred to individual observation chambers and number of writhes (constriction of abdomen, turning of trunk, and extension of hind Limbs) were monitored over the following 20 minutes, beginning 3 min after the injection of acetic acid. At the end of observation period the animals were killed by cervical dislocation and exsaguination. The average number of writhes in each group of drug treated mice was compared with that of the control group and degree of analgesia was expressed as % inhibition calculated from the equation:

$$\% \text{ Inhibition} = (1 - N_t/N_c) \times 100$$

Where, $N_c$=number of writhes in control
$N_t$=number of writhes in drug treated mice

TABLE 1

Analgesic of paracetamol (1) and NO-NSAIDs (12 and 13)

| COMPOUND | % INHIBITION IN WRITHINGS |
|---|---|
| 1 | 45.36 ± 1.34 |
| 10 | 13.52 ± 1.82# |
| 12 | 58.35 ± 1.50# |
| 11 | 17.24 ± .41# |
| 13 | 61.80 ± 1.69# |

Results are expressed as mean ± standard error of mean (SEM).
indicates P < 0.05 w.r.t. Paracetamol (100 mg/kg p.o.)

O-alkylated NO-releasing derivatives 12 and 13 of paracetamol (1) exhibited better response than the parent drug indicated by greater % inhibition in writings. The % inhibition in case of 12 and 13 (58.35±1.50, 61.80±1.69 respectively) was found to be better than paracetamol (1) which was 45.36±1.34. The intermediates 10 and 11, having terminal Br (which was later converted to —$ONO_2$ moiety on treatment with $AgNO_3$) showed very negligible % inhibition in writings indicating that NO release is responsible for better analgesic activity of the compounds 0.12 and 13 (having NO releasing —$ONO_2$) moiety.

Biochemical Assays (Table 3 and FIG. 2 Sheet No. 1 for SGPT(ALT), and Table 4 and FIG. 3 Sheet No. 2 for ALP): Paracetamol was given at a dose of 1000 mg/Kg and an equivalent dose of 1000 mg/Kg of the derivatives 12 and 13 was given p.o. Before administration blood samples of each animal were taken and after 6 hrs the animals were sacrificed to collect blood samples, and the serum was separated out. Measurement of plasma markers of liver Serum Glutamate oxaloacetate transaminase (SGOT) pyruvate transaminase (SGPT) and Alkaline Phosphatase (ALP) were assayed spectrophotometrically using commercially available kits.

The animals were divided into different groups containing 6-8 animals in each group. Animals were lightly anaesthetized with diethyl ether and blood samples were collected which served as the basal reading of the enzyme to be analyzed. These groups of rats were then treated with paracetamol (1000 mg/Kg, i.p.), and equivalent dose of the test compounds. Control group was treated with an equal volume of vehicle (0.9% w/v sodium chloride containing 20% v/v tween-80). Animals were lightly anesthetized with ethyl ether and blood samples were collected and allowed to coagulate at room temperature for 1 hr, serum was then separated by centrifugation (5,000 rpm for 10 min) at 4° C. and stored at −40.0° C. till estimation. Plasma markers of liver injury were assayed spectrophotometrically using following commercially available kits according to standard laboratory techniques:

TABLE 3

% increase in SGPT/ALT level

| COMPOUND | % INCREASE IN SGPT/ALT LEVEL |
|---|---|
| CONTROL | 2.92 ± 0.3* |
| Paracetamol (1) | 83.11 ± 3.3# |
| 12 | 27.94 ± 2.7*,# |
| 13 | 11.72 ± 1.4*,# |

Results are expressed as mean ± standard error of mean (SEM).
*indicates $P < 0.05$ w.r.t. control (0.5% sodium CMC); and,
indicates $P < 0.05$ w.r.t. paracetamol (1000 mg/kg, i.p.)

TABLE 4

% increase in ALP level

| COMPOUND | % INCREASE IN ALP LEVEL |
|---|---|
| CONTROL | 1.05 ± 0.49* |
| Paracetamol (1) | 15.75 ± 1.07# |
| 12 | 4.17 ± 0.62* |
| 13 | 2.85 ± 0.83* |

Results are expressed as mean ± standard error of mean (SEM).
*indicates $P < 0.05$ w.r.t. control (0.5% sodium CMC); and,
indicates $P < 0.05$ w.r.t. paracetamol (1000 mg/kg, i.p.)

Overproduction of this toxic metabolite 2 leads to depletion of glutathione stores in liver and further accumulation of the toxic metabolite causes tissue injury and cell death. Enzymes like alkaline phosphatase (ALP, EC 3.1.3.1), serum glutamate pyruvate transaminase (SGPT) or alanine aminotransferase (ALT) (EC 2.612) and the total proteins are considered as plasma markers of liver injury. Nitric oxide releasing paracetamol derivatives 12 and 13 were evaluated for their effect on the markers of liver injury like enzymes ALP and SGPT/ALT. The plasma level of these enzymes is found to increase in the case of liver toxicity. The graph indicates that the rise (with comparison to the basal value) in the case of 1 is much more than in the case of NO releasing derivatives 12 and 13, showing that they cause lesser liver toxicity than the parent drug paracetamol 1.

Histopathology (FIG. 5 Sheet No. 3) For liver histopathology, the livers were removed and portions were fixed in 10% buffered formalin (pH 7.4). They were then processed by standard histopathological techniques, stained with Haematoxylin and Eosin (H&E), and examined for morphologic evaluation for liver injury.[21]

Light microscopic analysis of liver samples obtained from mouse treated with control (0.9% w/v sodium chloride containing 20% v/v tween-80), paracetamol (1), 12 and 13, at a dose of 1000 mg/kg, i.p. is shown in sections (A), (B), (C), and (D) respectively. The interpreted results obtained from histopathological studies are summarized below:

(i) Control did not cause any damage to the liver. Only mild portal triad inflammation was observed.

(ii) Paracetamol (1) a proven liver toxic caused ballooning degeneration, sinusoidal decongestion, portal triad inflammation and spoty necrosis in Zone I.

(iii) Just mild ballooning degeneration was observed in the case of 12.

(iv) Compound 13 also didn't cause any significant damage to the liver.

These results were supportive in summarizing that NO-release counteracts the liver toxic side effects of paracetamol (1).

Nitric Oxide Release {Table 5 and FIG. 4 Sheet No. 2, FIG. 5}:

100 mg/Kg of the derivatives 12 and 13 was given p.o. After 6 hours the animals were sacrificed to collect blood samples and the serum was separated out to find out the levels of NO. Plasma nitrate/nitrite concentration level was measured by commercially available Cayman Kit.

TABLE 4

% increase in ALP level

| COMPOUND | NITRATE CONCENTRATION (µmol/l) |
|---|---|
| CONTROL | 182.1 ± 0.68 |
| 12 | 354.2 ± 2.17# |
| 13 | 265.4 ± 2.47# |

Results are expressed as mean ± standard error of mean (SEM).
*indicates $P < 0.05$ w.r.t. control (0.5% sodium CMC)

After a period of 6 hr 12 and 13, NO-releasing derivatives showed increase in % NO serum level w.r.t. control. The NO release of these compounds could be the acting force behind their better analgesic and anti-inflammatory activities than the parent drug.

In vitro cox-2 (ovine) inhibitory assay: The prostaglandin product is quantified via enzyme immunoassay (EIA) using a broadly specific antibody that binds to all major prostaglandin compounds. Assay kit was purchased from Cayman Chemical Company, USA.

Celecoxib: 79.0% (positive control)

PCM: 24.0%

12: 21.0%

13: 32.5%

Our compound 13 has shown to have better COX-2 (in vitro) than the parent drug paracetamol. The data of analgesic and anti-inflammatory activities is exactly complimenting and supporting it. The NO-releasing should have been found to have better peripheral analgesic activity and significant anti-inflammatory activity as compared to the parent drug. The derivatives were found to release NO in vivo and are devoid of liver toxicity as indicated by serum lesser increase in serum GPT(ALT) and ALP levels and histopathological studies. Moreover, 13 showed better COX-2 (ovine) binding activity than the parent drug. On the whole more effective and less toxic derivatives of 1 have been synthesised. The advantages of the present investigation are that these NO releasing compounds have shown better analgesic and anti inflammatory activity than the parent drug, and less liver toxicity in biochemical and histopathological studies.

The present invention deals with ether derivatives of paracetamol (1), whereas the prior art has ester derivatives. The rate of release of NO will be different than the prior art.

We claim:

1. A compound of general formula A

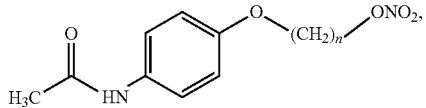

Formula A wherein the value of n is selected from 2 to 5.

2. The compound according to claim 1 selected from the group consisting of

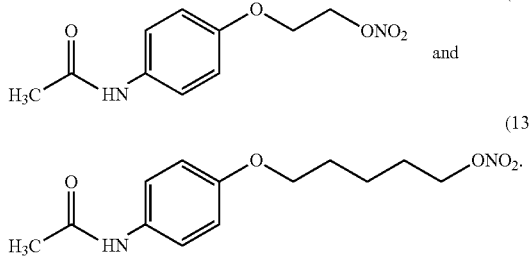

3. The compound according to claim 1 selected from the group consisting of compounds of the general formula comprising:
   (i) N-[4-(2-Nitrooxy-ethoxy)-phenyl]-acetamide (12);
   (ii) N-[4-(S-Nitrooxy-pentoxy)-phenyl]-acetamide (13);
   (iii) N-[4-(3-Nitrooxy-propoxy)-phenyl]-acetamide (18); and
   (iv) N-[4-(4-Nitrooxy-butoxy)-phenyl]-acetamide (19).

4. The compound according to claim 1 wherein the compound of formula A is having better peripheral analgesic activity and significant anti-inflammatory activity as compared to paracetamol.

5. The compound according to claim 1 wherein the compounds possess better analgesic and anti inflammatory activity and devoid of toxicity as compared to the parent drug paracetamol (1).

6. The compound according to claim 1 wherein the compound N-[4-(2-nitrooxy-ethoxy)-phenyl]-acetamide (12) and compound N-[4-(5-nitrooxy-pentoxy)-phenyl]acetamide (13) showed 32.68±1.45% and 31.15±1.31% at 2 hr, and, 26.44±0.10% and 28.45±1.28% at 4 hr increase respectively, in the paw volume as compared to 38.37±1:1.26% and 58.92±1:1.56% (at 2 hr and 4 hr respectively) in case of paracetamol at a dose of 100 mg/kg body weight.

7. The compound according to claim 1 wherein the compound N-[4-(2-nitrooxy-ethoxy)-phenyl]-acetamide (12) and compound N-[4-(5-nitrooxy-pentoxy)-phenyl]acetamide (13) showed increase in NO serum level 354.2±2.17 and 265.4±2.47 respectively with respect to control (182.1±0.68) at a dose of 100 mg/kg body weight.

8. The compound according to claim 1 wherein the compound N-[4-(5-nitrooxy-pentoxy)-phenyl]acetamide (13) showed in vitro cox-2 (ovine) inhibitory activity 32.5% as compared to control 24.0%.

9. The process for preparation of a compound of general formula A

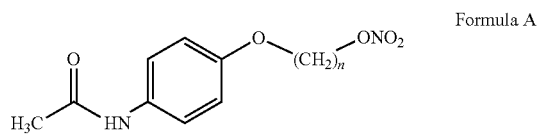

Formula A wherein the value of n is selected from 2-5 comprising the steps
   a) reacting paraeetamol with dibromo alkane in an organic solvent in presence of alkali carbonate for a period up to 12 hours,
   b) filtering the reaction mixture followed by evaporation of solvent to obtain solid residue,
   c) dissolving the residue in water immisible solvent and washing with sodium hydroxide solution followed by washing with water, evaporating the solvent to O-alkylated bromo derivative of paracetamol,
   d) reacting the O-alkylated bromo derivative of paracetamol with sliver nitrate under reflux in an aprotic solvent up to 12 hours, further filtering and evaporating the filtrate to obtain the nitrate esters derivative of paracetamol of general formula A wherein the value of n is selected from 2-5.

10. The process according to claim 9, wherein the dibromoalkane is selected from a group consisting of 1,2-dibromoethane, 1,3-dibromopropane, 1,4-dibromobutane and 1,5-dibromopentane.

11. The process according to claim 9 wherein the organic solvent used is selected from a group consisting of ethyl methyl ketone, acetone, acetonitrile and mixture thereof.

12. The process according to claim 9; wherein the aprotic solvent used is selected from a group consisting of acetonitrile, benzene, hexane and mixture thereof.

13. The pharmaceutical composition comprising the compounds of general formula A of claim 1, and pharmaceutically acceptable excipients.

* * * * *